United States Patent [19]

Navis

[11] Patent Number: 5,676,159
[45] Date of Patent: Oct. 14, 1997

[54] ULTRASOUND COVER

[75] Inventor: John A. Navis, Naperville, Ill.

[73] Assignee: Janin Group, Aurora, Ill.

[21] Appl. No.: 743,304

[22] Filed: Nov. 5, 1996

[51] Int. Cl.$^6$ .................................................. A61F 5/37
[52] U.S. Cl. .......................... 128/846; 128/849; 128/856
[58] Field of Search ..................... 128/849–856, 128/662.06

[56] References Cited

U.S. PATENT DOCUMENTS

| | | |
|---|---|---|
| 4,392,853 | 7/1983 | Muto . |
| 4,473,073 | 9/1984 | Darnell . |
| 4,552,196 | 11/1985 | Cunningham et al. . |
| 4,634,433 | 1/1987 | Osborne . |
| 4,887,615 | 12/1989 | Taylor ................................ 128/856 |
| 5,148,940 | 9/1992 | Mendise . |
| 5,168,863 | 12/1992 | Kurtzer . |
| 5,174,276 | 12/1992 | Crockard . |
| 5,325,846 | 7/1994 | Szabo . |
| 5,433,221 | 7/1995 | Adair ................................ 128/856 |
| 5,469,853 | 11/1995 | Law ................................ 128/662.06 |
| 5,490,524 | 2/1996 | Williams ............................. 128/856 |

OTHER PUBLICATIONS

*Microtek's Ultrasound Probe Drapes* by Microtek Medical, Inc., Columbus, Ohio dated 1993—Advertising flyer.
*Ultrasound Transducer Covers and Needle Guides* by Civco Medical Instruments, undated—Advertising brochure.
*The Modular Color Doppler System* (System 3535) by B & K Medical, undated—Advertising flyer.

*Primary Examiner*—Michael A. Brown
*Attorney, Agent, or Firm*—Lee, Mann, Smith McWilliams, Sweeney & Ohlson

[57] ABSTRACT

A flexible polyurethane cover with a closed end that is contact clear for establishing sterility while using an ultrasound probe. The cover has gel prepositioned inside the contact clear polyurethane closed end. A drape can be attached to the contact clear cover. A method of making such a cover including folding a contact clear polyurethane sheet over itself and securing the side edges to form a compartment with a closed end, inverting the cover as necessary to position the seams inside the cover, applying a gel into the closed end portion of the cover, and sterilizing the cover without affecting the gel by applying a dry heat in a slow persistent manner after the gel is already in the cover.

16 Claims, 1 Drawing Sheet

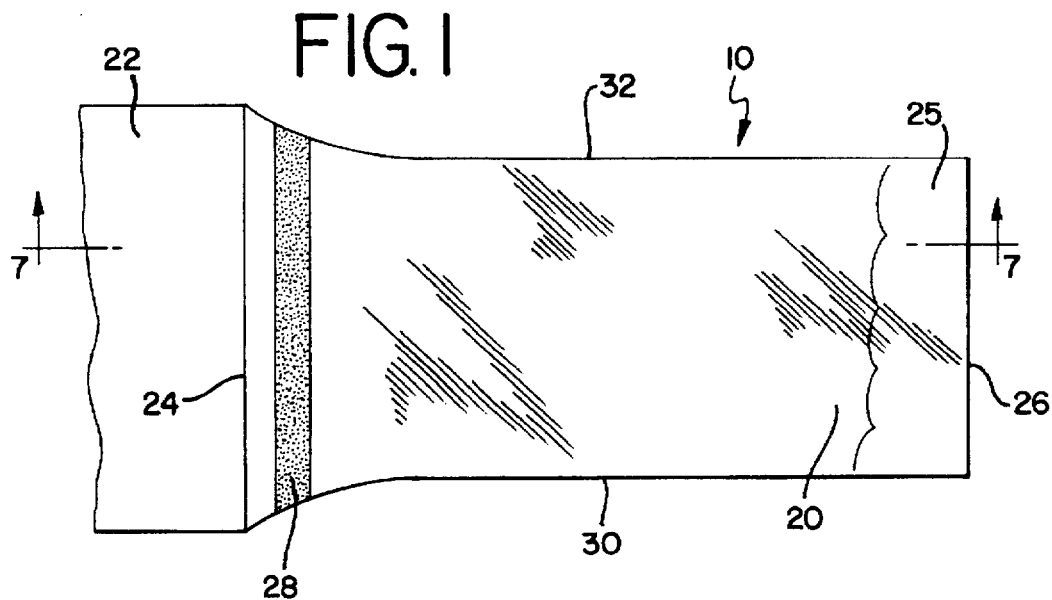
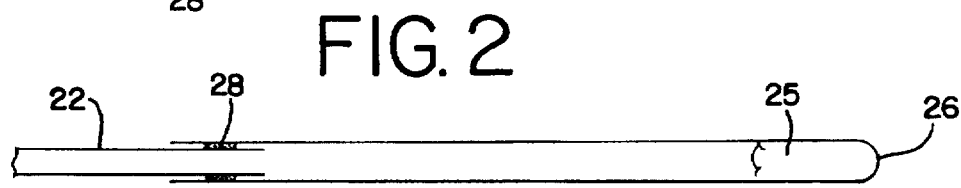
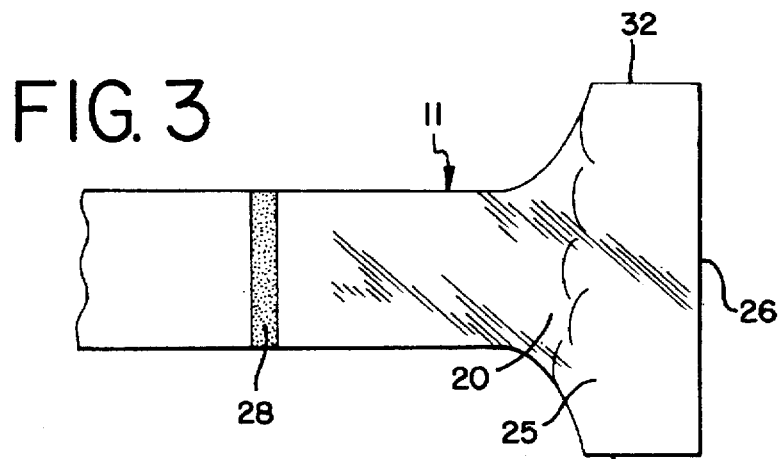
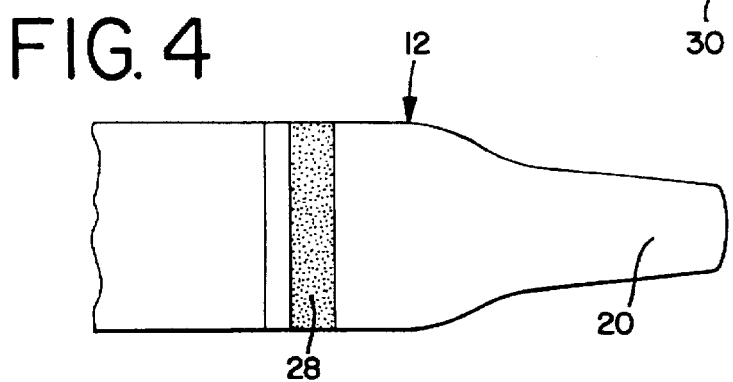

ULTRASOUND COVER

BACKGROUND OF THE INVENTION

The invention generally relates to covers for an ultrasound probe and a method of making the same. Specifically, the invention entails a cover that has gel pre-positioned inside the contact clear polyurethane closed end portion and is ready for use upon removal from its package.

The prior art U.S. Pat. No. 4,887,615 is directed to a sterilized drape for draping an ultrasound probe. A drape is used for enclosing an ultrasound probe to assure sterility during invasive ultrasound procedures. The drape includes an elongated sleeve member formed of a sterilizable, flexible, fluid impervious material with an open first end and substantially closed second end having a circular fenestration therethrough. A tubular member having an open first end, a closed second end, and a diameter substantially equal to the diameter of the sleeve member fenestration extends from and is sealingly fastened to the substantially closed end of the sleeve member, with the tubular member open end communicating with the sleeve interior through the sleeve member fenestration.

The drape shown in '615 patent is different from the present invention since it describes a minimum of four components to be used. One component is a rectangular piece of sterilizable, flexible, fluid impervious material. The piece has a fenestration cut centrally through it. A tubular member extends through the fenestration and has an open end and closed end. Ultimately, the ultrasound probe would be received in the elongate portion of the tube. The closed end is affixed to the fenestration of the rectangular piece by means of a toroidal-shaped piece of double-sided adhesive. Thus, the tubular member is sealed against the rectangular piece. The piece is then heat sealed along marginal edges. The piece is then joined to an elongate tubular portion. The present invention avoids the inefficiency of requiring a circular fenestration in the polyurethane length of material. Further, the end of the present embodiment is always fully closed. Significantly, the '615 cover does not disclose prepositioning a gel inside the closed end portion of the cover. Such a prepositioned gel saves the doctor a step prior to using the cover. Finally, the '615 patent does not have optical clarity features or the ability to see the probe through the closed end portion of the cover. Such an ability to see that the probe is in contact with the gel is beneficial to a doctor. The gel is necessary for the doctor to ensure proper/ adequate contact between the gel and the ultrasound probe head and between the probe head and the closed end portion of the cover.

Accordingly, it would be desirable to provide a contact clear cover that can be used to maintain sterility while using an ultrasound probe that is ready for use upon removal from the package. The present invention has a gel, which is required with many ultrasound probes, pre-positioned in a contact clear closed end portion of a cover.

In connection with the foregoing objectives. Them is no need for a practitioner to apply a gel inside the cover. The gel is already located where the doctor wants it to be. Therefore, before using the cover, there is no need for an extra step of inserting the gel in the cover or putting a gel on the head of the transducer of the probe. This saves using a long insertion nozzle or a less effective method of affixing the gel to the probe before placing it in the cover. The gel is in the sterilized closed end portion of the cover, which is ready to use.

It is also a goal of the invention to provide a cover that is polyurethane, which is less rigid than polyethylene covers. Also, polyethylene has a tendency to wrinkle; whereas, polyurethane will remain smooth during use.

Further, it is another intention of the invention to provide a cover that is supple, pleasant to touch and durable. The covers can be made in specific sizes for each probe to closely fit over the transducer head. There is no oversized closed end piece or excess material that may be required while using a cover that does not have a gel pre-positioned in the closed end.

Moreover, an additional achievement of the cover is that it is contact clear, which gives the ability to see the acoustic gel that is applied inside the cover to ensure that the probe head of the ultrasound transducer is in contact with the gel. This allows for additional control and better direction of the head for improved viewing during an ultrasound procedure.

Further aspects and benefits of the invention will be appreciated by those practicing in the medical field.

SUMMARY OF THE INVENTION

The present invention is a cover that has acoustic gel pre-positioned in the closed end portion of the cover that is primarily for use with an ultrasound probe. The invention additionally provides for the closed end to be contact clear so that contact of the probe's transducer with the gel is readily verified prior to and during use.

BRIEF DESCRIPTION OF THE DRAWINGS

FIG. 1 is a top view of a preferred embodiment;

FIG. 2 shows a side view of the embodiment of FIG. 1 taken along line 7—7;

FIG. 3 shows a top view of an alternate embodiment.

FIG. 4 shows a top view of an alternate embodiment.

DETAILED DESCRIPTION OF THE INVENTION

The invention is a flexible cover with a polyurethane closed end that is contact clear and maintains sterility while using an ultrasound probe. The cover has gel pre-positioned inside the polyurethane closed end.

In the Figures, like reference numerals indicate the same elements throughout. Reference numerals 10 and 11 and 12, respectively denote the basic cover and two exemplary optional alternatives of that embodiment.

In greater detail, with reference to FIGS. 1 and 2, a cover 10 embodying the invention is illustrated. The cover 10 comprises a closed-end portion 20 and a drape 22 connected at a proximal end 24 opposite to the closed-end portion 20. The closed-end portion 20 and drape 22 are connected at fastening area 28. The closed-end portion 20, which is associated with the ultrasound probe, is contact clear.

More specifically, the closed-end portion 20 is a folded polyurethane sheet that is contact clear. It can be made of the desired size and suppleness to be used with various probes. The thickness of the polyurethane sheet ranges from about 0.5 mil (0.0005 inch) to about 3.5 mils (0.0035 inch). About 1.5 to 2 mils has been found to be optimal, being thick enough not to tear and thin enough for easiest use. Polyurethane less than 0.5 mil has a tendency to tear, and polyurethane thicker than 3.5 mils is too thick to be practical. A commercially available source is J. P. Stevens, Conn., product #1400. The closed-end portion 20 is constructed by folding a polyurethane sheet over itself and bonding the side ends.

The closed-end portion 20 is folded at peripheral edge 26. A gel 25 is pre-positioned along peripheral edge 26. The closed-end portion 20 has a gel 25 coveting the section of the portion 20 that the probe contacts during normal operation.

The closed-end portion 20 is sealed at side edges 30 and 32 of the folded sheet. The side edges 30 and 32 are the only parts of the closed-end portion 20 that is not contact clear. Preferably, the side edges 30 and 32 can be made with a wire ribbon seal, but any other style seal may be used.

The homogeneous polyurethane sheet folded over itself forms a receptacle inside side edges 30 and 32 to retain an ultrasound probe. The peripheral edge 26 is the intended location for full insertion of a probe.

In a preferred embodiment, the closed-end portion 20 is structured so that the edges 26, 30, and 32 conform to the shape of the probe. This minimizes excess material that may make use of the cover more difficult.

In addition, the seams of side edges 30 and 32 may be on the outside of the cover 10 or they may be inside of cover 10, which is preferred. Having the seams of side edges 30 and 32 on the inside is accomplished by inverting the cover 10 prior to attaching it to the drape 22, which prevents any seams from contacting, injuring, or irritating a patient's tissue during the ultrasound procedure.

The drape 22 of the preferred embodiment can be made of a non-static polyethylene flat tube of varying widths and the desired length. The tube forming drape 22 may be extruded as a tube or it may be a flat sheet folded over itself and sealed on one side. Alternately, the drape 22 can be made of two flat sheets affixed together. The drape 22 can be a semi-translucent material. The drape 22 can be made of non-static polyethylene, preferably approximately 2 mil thick. The drape 22 is a tube to enclose wires or cable extending from the probe.

The proximal end 24 opposite the closed-end portion 20 and the drape 22 can be heat sealed together if the materials of the sheets are compatible or adhered by double face tape if the sheets are incompatible. Such tape is preferred in fastening a polyurethane closed-end portion and a polyethylene drape. There are a wide variety of medical grade double face tapes well known in the medical arts that are acceptable for such use.

FIG. 3 provides an alternate construction of the closed-end portion 20. The embodiment for the cover 10 shown in FIG. 1 is similar to cover 11 of FIG. 3, except that the cover 11 is constructed for a different type of probe. It is constructed so that a probe with a wide transducer head can be rotated into the cover 11.

FIG. 4 provides an additional alternate construction of the closed-end portion 20. The embodiment for the cover 10 shown in FIG. 1 is similar to cover 12 of FIG. 4, except that the cover 12 is constructed for a different type of probe. It is constructed so that a probe with a narrow transducer head can be used with the cover 12. The length and width of the closed-end portion 20 can vary to accommodate different sized probes used with this embodiment.

The method of making cover 10 begins with selecting a contact clear polyurethane sheet. The sheet is folded over itself. Then it is either heat sealed by a wire ribbon seal or other method of heat sealing, thereby forming the side edges 30 and 32. Use of a wire ribbon seal is preferred as it will make a strong, thin seal. This makes a compartment that will ultimately cover the transducer of the probe.

Next, a drape 22, as described above, can be attached to the compartment at the proximal end 24 opposite the closed-end portion 20. The preferred method of fastening a polyurethane closed-end portion and a polyethylene drape is using a double sided tape. Other methods such as heat sealing are acceptable if the materials used for the compartment and the drape are compatible.

A gel 25 is inserted into the cover 10 using a long nozzle to place the gel 25 at the peripheral edge 26 of the closed end portion 20 and extend away from the peripheral edge 26 as far as required to provide a volume of gel 25 necessary for the probe to properly function. Alternately, for certain applications the gel 25 can be applied to the closed-end portion 20 while the cover 10 is inside-out by applying it directly to the surface of the closed end portion 20. The inside-out cover can be made that way, which may allow seams to be on the inside of the cover when turned outside out, or the cover 10 can be turned inside-out for the purpose of applying the gel 25.

The method includes the step of sterilizing the cover 10 without affecting the gel 25. Sterilization by radiation can break down a gel. Using a gas can be problematic since certain gases, such as EtO, can be absorbed by a gel. The preferred method is providing a dry heat that is applied in a slow persistent method while the gel 25 is already in place. The preferred method does not adversely affect the cover 10 or the gel 25.

An optional step of inverting the cover 10 before attaching it to the drape 22 can be performed so that any effects of the heat sealing, i.e. a seam, can be positioned inside the cover 10. Having the seams of side edges 30 and 32 on the inside prevents any seams from contacting, injuring, or irritating a patient's tissue during the ultrasound procedure.

Preferably the drape is telescopically folded to a prepackage size before sterilization. The sterilized cover 10 is placed into a package to maintain the sterility.

Alternate Embodiments

The exact dimensions or proportions of the preferred embodiment and the alternate embodiment are not critical to the invention. The suppleness, structure, and size of the cover can be made to the dimension required for a particular probe. It will also be appreciated that although the invention has been disclosed with reference to certain probes, it encompasses covers for similar instruments of different sizes and shapes. Further, an entire family of ultrasound covers can be produced based on the disclosed structure, technology, and method.

Achievements

Accordingly, an improved cover that has a gel positioned in the closed end for use with an ultrasound probe is disclosed herein. The closed end is contact clear for easy sight-positioning of the probe with respect to the gel. While the invention has been described in connection with preferred embodiments for the cover, a range of equivalents are encompassed by the scope of the claims appended hereto.

What is claimed is:

1. A flexible cover for establishing sterility of an ultrasound probe to be inserted therein, the cover comprising a proximal end, a polyurethane closed end portion being contact clear, and a gel prepositioned inside the polyurethane closed end portion.

2. The cover of claim 1 wherein the closed-end portion is folded at a peripheral edge, the gel being applied along the peripheral edge.

3. The cover of claim 2 having side edges formed from the folded closed-end portion wherein the side edges are sealed.

4. The cover of claim 3 wherein the side edges are heat sealed with a wire ribbon.

5. The cover of claim 1 wherein the polyurethane is between 0.5 mil and 3.5 mil thick.

6. The cover of claim 5 wherein the polyurethane is about 2 mil thick.

7. The cover of claim 1 including a drape fastened to the proximal end opposite the closed-end portion.

8. The cover of claim 7 wherein the drape is constructed of non-static polyethylene and the closed-end portion is constructed of non-static polyurethane.

9. A flexible cover for establishing sterility of an ultrasound probe to be inserted therein, the cover comprising:

a polyurethane closed-end portion that is contact clear, a proximal end opposite the closed-end portion, a gel prepositioned inside the polyurethane closed end portion, and a drape fastened to the proximal end;

wherein the closed-end portion is folded at a peripheral edge, the gel being applied along the peripheral edge.

10. The cover of claim 9 wherein the drape is an extruded, seamless tube.

11. The cover of claim 9 having side edges formed from the folded closed-end portion wherein the side edges are sealed along a seam, wherein the cover is inverted so that the seam is on the inside of the cover.

12. A method of making a flexible cover primarily for use with establishing sterility of an ultrasound probe, the method comprises the steps of:

folding a contact clear polyurethane sheet over itself, securing the folded sheet to form side edges and a compartment with a closed end portion, placing a gel into the closed end portion of the cover, sterilizing the cover and gel by dry heating.

13. The method of claim 12 including the additional steps of telescopically folding the cover to its prepackage size before sterilization and placing the sterilized cover into a package to maintain the sterility after sterilization of the cover.

14. The method of claim 12 wherein the step of securing the folded sheet portions along side edges consists of heat sealing the side edges.

15. The method of claim 14 including the additional step of attaching a drape to the compartment opposite the closed end portion.

16. The method of claim 15 including the additional step of inverting the cover before attaching it to the drape so that any effects of the heat sealing can be positioned in side the cover.

* * * * *

UNITED STATES PATENT AND TRADEMARK OFFICE
CERTIFICATE OF CORRECTION

PATENT NO. : 5,676,159
DATED : October 14, 1997
INVENTOR(S) : John A. Navis

It is certified that error appears in the above-indentified patent and that said Letters Patent is hereby corrected as shown below:

In column 1, line 56, "Them" should be "There".

Signed and Sealed this

Sixteenth Day of December, 1997

Attest:

BRUCE LEHMAN

*Attesting Officer*        *Commissioner of Patents and Trademarks*